(12) United States Patent
Guttag

(10) Patent No.: US 6,368,615 B1
(45) Date of Patent: Apr. 9, 2002

(54) CONTACT LENS HAVING A PHARMACEUTICAL AGENT RELEASABLY DISPOSED THEREIN

(76) Inventor: Alvin Guttag, 10921 Reed Hartman Hwy., Suite 316, Cincinnati, OH (US) 45242

( * ) Notice: Subject to any disclaimer, the term of this patent is extended or adjusted under 35 U.S.C. 154(b) by 0 days.

(21) Appl. No.: 09/422,247

(22) Filed: Oct. 21, 1999

Related U.S. Application Data

(62) Division of application No. 08/970,583, filed on Nov. 14, 1997, now Pat. No. 6,037,338, which is a division of application No. 08/785,979, filed on Jan. 21, 1997, now Pat. No. 5,910,511, which is a division of application No. 08/224,718, filed on Apr. 8, 1994, now Pat. No. 5,760,261, which is a continuation-in-part of application No. 07/853,428, filed on Mar. 18, 1992, now Pat. No. 5,346,929, which is a division of application No. 07/486,217, filed on Feb. 28, 1990, now Pat. No. 5,120,089.

(51) Int. Cl.[7] ............................. A61K 9/00; A61K 9/14; A61F 2/00; A01N 37/36; G02C 7/04
(52) U.S. Cl. ...................... 424/429; 424/427; 424/486; 514/159; 514/165; 351/160 R
(58) Field of Search ................................. 424/429, 427, 424/486; 351/160 R; 514/165

(56) References Cited

U.S. PATENT DOCUMENTS

| | | | |
|---|---|---|---|
| 656,435 A | | 8/1900 | Bonhoeffer |
| 1,122,201 A | | 12/1914 | Hiemenz |
| 1,338,297 A | | 4/1920 | Gruttefien |
| 1,689,696 A | | 10/1928 | Summers |
| 4,136,250 A | * | 1/1979 | Mueller et al. ......... 351/160 R |
| 4,447,562 A | * | 5/1984 | Ivani ....................... 514/772.5 |
| 4,713,244 A | * | 12/1987 | Bawa et al. ................. 424/429 |
| 5,035,884 A | * | 7/1991 | Song et al. ............... 424/78.06 |
| 5,300,287 A | * | 4/1994 | Park ......................... 424/78.04 |
| 5,965,631 A | * | 10/1999 | Nicolson et al. ............ 523/106 |
| 6,027,745 A | * | 2/2000 | Nakada et al. ............... 424/427 |
| 6,156,244 A | * | 12/2000 | Muller et al. ................. 264/2.6 |
| 6,218,463 B1 | * | 4/2001 | Molock et al. ............. 524/720 |

FOREIGN PATENT DOCUMENTS

| | | |
|---|---|---|
| CS | 158430 | 6/1975 |

OTHER PUBLICATIONS

Gu et al. Studies on the Hydrolysis of Biocompatible Acrylic Polymers having Aspirin–Moieties. Biomaterials Medical Devices, and Artificial Organs. 11(2–3). Pp. 211–219, 1983.*
Lide, Physical Constants of Organic Compounds, CRC Handbook of Chemistry and Physics, 1991–92 72nd Edition, pp. 3–457.
Pala et al, J. Med. Chem., vol. 11, No. 4, pp. 910–911, 1968.
Maruko Phar. Co., Chemical Abstract, vol. 94, pp. 544,1981, 46974q.
Hrabak et al., Chemical Abstract, vol. 84 pp. 430, 1976, 16972p.

* cited by examiner

*Primary Examiner*—Michael G. Hartley
*Assistant Examiner*—Michael A. Willis
(74) *Attorney, Agent, or Firm*—Eric W. Guttag; Smith, Guttag & Bolin

(57) ABSTRACT

A contact lens having a pharmaceutical agent releasably disposed therein. The lens itself comprises a polymer of an unsaturated carboxylic acid ester of salicylic acid, the unsaturated carboxylic acid having up to 24 carbon atoms and 1–4 ethylenic double bonds, or a pharmaceutically acceptable salt of the salicylic acid ester.

14 Claims, No Drawings

CONTACT LENS HAVING A PHARMACEUTICAL AGENT RELEASABLY DISPOSED THEREIN

RELATED APPLICATIONS

This is a divisional of U.S. application Ser. No. 08/970,583, filed Nov. 14, 1997, U.S. Pat. No. 6,037,338, which is a divisional of U.S. application Ser. No. 08/785,979, filed Jan. 21, 1997, now U.S. Pat. No. 5,910,511 issued Jun. 8, 1999, which is a divisional of U.S. application Ser. No. 08/224,718, filed Apr. 8, 1994, now U.S. Pat. No. 5,760,261 issued Jun. 2, 1998, which is a continuation-in-part of U.S. application Ser. No. 07/853,428, filed Mar. 18, 1992, now U.S. Pat. No. 5,346,929 issued Sep. 13, 1994, which is a divisional of U.S. application Ser. 07/486,217, filed Feb. 28, 1990, now U.S. Pat. No. 5,120,089 issued Jun. 9, 1992, the entire disclosures of which are hereby incorporated by reference and relied upon.

BACKGROUND OF THE INVENTION

1. Field of the Invention

The present invention relates to a method of treating an aspirin-treatable condition. The present invention further relates to a compound and a pharmaceutical composition for use in treating an aspirin-treatable -condition.

2. Background Information

Aspirin (acetylsalicylic acid), one of the oldest over-the-counter drugs having been marketed since 1899, continues to be used for relief from headaches, fevers and arthritis pain. Aspirin works as an analgesic to reduce pain, an anti-pyretic to reduce fever and an anti-inflammatory agent. Recently, aspirin has been shown to aid in the prevention of heart attacks. However, aspirin does have undesirable side effects. Use of aspirin has been linked to Reye's Syndrome in children, hearing impairment in heavy users, stomach problems, excessive bleeding and certain rare but serious complications of pregnancy.

Other anti-inflammatory drugs that reduce pain such as acetaminophen (Tylenol) and ibuprofen (Motrin, Advil and Nuprin) are also available. However, these also are associated with potentially harmful side effects. Acetaminophen, the most preferred analgesic after aspirin, can cause delayed liver damage when used excessively and major kidney damage with long-term chronic use.

SUMMARY OF THE INVENTION

Accordingly, it is an object of the present invention to provide an alternative to aspirin which has lesser undesirable side effects associated with aspirin.

Further objects and advantages of the present invention will be clear to one skilled in the art from the description that follows.

In one embodiment, the present invention relates to a method of treating an aspirin-treatable condition other than gout by administering to a mammal in need of such treatment an amount sufficient to effect said treatment of a compound of Formula I

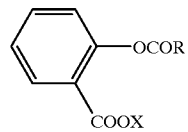

wherein R is an alkyl group (straight chain or branched chain) of at least two carbon atoms, an alkenyl group, (straight chain or branched chain), an aryl group; and X is hydrogen or a pharmaceutically acceptable salt thereof, e.g., where X is a non-toxic metal or ammonium.

Aspirin-treatable conditions include, but are not limited to, pain such as headache and arthritis pain, fever, pre-eclampsia, and especially heart attacks and predisposition of heart attack.

In another embodiment, the present invention relates to a compound of Formula I wherein R is an alkyl group (straight chain or branched chain) of at least 6 carbon atoms, an alkenyl group (straight chain or branched chain) of 2 to 17 carbon atoms, an aryl group; or a pharmaceutically acceptable salt thereof.

In another embodiment, the present invention relates to a compound of Formula I wherein R is an alkyl group (straight chain or branched chain) of at least 6 carbon atoms, an alkenyl group (straight chain or branched chain) of 2 to 23 carbon atoms, an aryl group; or a pharmaceutically acceptable salt thereof.

In a further embodiment, the present invention relates to a pharmaceutical composition for use in treating an aspirin-treatable condition comprising a compound of Formula I wherein R is an alkyl group (straight chain or branched chain) of at least 2 carbon atoms, an alkenyl group (straight chain or branched chain) of 2 to 17 carbon atoms, an aryl group, or a pharmaceutically acceptable salt thereof, in an amount sufficient to effect treatment of said condition, together with a pharmaceutically acceptable carrier.

In a further embodiment, the present invention relates to a pharmaceutical composition for use in treating an aspirin-treatable condition comprising a compound of Formula I wherein R is an alkyl group (straight chain or branched chain) of at least 5, e.g., 6 to 23 or 17 to 23, carbon atoms, an alkenyl group (straight chain or branched chain) of 2 to 23 carbon atoms, an aryl group, or a pharmaceutically acceptable salt thereof, in an amount sufficient to effect treatment of said condition, together with a pharmaceutically acceptable carrier.

DETAILED DESCRIPTION OF THE INVENTION

The present invention relates to the use of compounds of the following Formula I

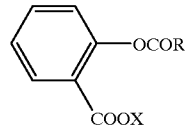

wherein R is an alkyl group (straight chain or branched chain) of 2 or more carbon atoms (advantageously, 2 to 17 carbon atoms) or an alkenyl group (straight chain or branched chain) of 2 to 23 carbon atoms, an aryl group (advantageously, phenyl), and X is hydrogen or a pharmaceutically acceptable salt forming metal or group (advantageously, sodium, potassium, lithium, calcium or ammonium salts). Of the compounds of Formula I, those in which R is unsaturated and those were R is saturated and contain more than 5 carbon atoms are believed to be disclosed for the first time herein. The compounds are solid white powders.

Compounds of Formula I to which the invention relates include, but are not limited to, propionylsalicylic acid and its sodium, potassium, lithium, ammonium and calcium salts; butyroylsalicyclic acid and its sodium, potassium, lithium, ammonium and calcium salts; valeroylsalicylic acid and its sodium, potassium and calcium salts; isovaleroyl-salicylic acid and its sodium, potassium, lithium, ammonium and calcium salts; caproyl salicylic acid and its sodium, potassium, lithium and calcium salts; heptanoyl salicylic acid and its sodium, potassium, lithium, calcium and ammonium salts; stearoyl-salicylic acid and its sodium, potassium, lithium and calcium salts; methacryloyl-salicylic acid and its sodium, potassium, lithium and calcium salts; crotonoyl-salicylic acid and its sodium, potassium and calcium salts; oleoylsalicylic acid and its sodium, potassium, lithium and calcium salts; the ammonium salt of propionylsalicylic acid; and the ammonium, sodium, calcium, potassium and lithium salts of acryloylsalicylic acid, as well as acryloylsalicylic acid itself.

Compounds of Formula I to which the invention also relates include, but are not limited to, unsaturated acid derivatives where the acid can have up to 24 carbon atoms, i.e., when R is alkenyl, it can be 2 to 23 carbon atoms. Illustrative examples of such salicylic acid esters include those from erucic acid (cis-13-docosenoic acid, R is 21), selacholeic acid (a 24 carbon atom cis alkenoic acid), palmitoleic acid (16 carbon atom unsaturated acid) and arachidonic acid (20 carbon atoms, R is 19 carbon atoms and having four double bonds).

Particularly preferred are erucocyl salicylic acid and its sodium, potassium, lithium, ammonium and calcium salts. As starting materials there can be used erucoyl chloride, bromide, iodide and anhydride. The primary source of erucic acid is rapeseed oil. About 50% of the glyceride esters in rapeseed oil are esters of erucic acid.

Compounds of Formula I to which the invention also relates include, but are not limited to, saturated acid derivatives where the acid can have up to 24 carbon atoms, i.e, when R is alkenyl, it can be 2 to 23 carbon atoms. Illustrative examples of such salicylic acid esters include those from arachidic acid, behenic acid and lignoceric acid.

The compounds of Formula I can be made in the same manner as aspirin, by conventional acylation procedures (other than the ketene procedure), for example, for typical procedures see U.S. Pat. No. 644,077; Bonhofer, U.S. Pat. No. 656,435; Hiemenz, U.S. Pat. No. 1,122,201; Gerngross, U.S. Pat. No. 1,217,862; Gruttefien, U.S. Pat. No. 1,338,297; Edmunds, U.S. Pat. Nos. 3,373,187 and 3,235,583; Berendes, U.S. Pat. Nos. 1,020,121 and 1,113,742; Richter, U.S. Pat. No. 1,058,904; Busch, U.S. Pat. Nos. 1,129,953 and 1,225,407; Allwey, U.S. Pat. No. 1,431,863; Lawrence, U.S. Pat. No. 2,003,374; Rothlenz, U.S. Pat. No. 2,052,663; Summus, U.S. Pat. No. 1,689,696; Stoesser, U.S. Pat. No. 2,987,539; Adams, U.S. Pat. No. 3,064,038; Schlosser, U.S. Pat. No. 3,109,019; Satzinger, U.S. Pat. No. 4,724,266; and Coleman, U.S. Pat. No. 2,207,611.

Conventional acylation procedures include reacting salicylic acid with the corresponding acyl halide, such as acyl chloride or the corresponding acid anhydride. Typical reactants include, but are not limited to, acryloyl chloride, methacryloyl chloride, propionyl chloride, stearoyl chloride, oleoyl chloride, propionic anhydride, butyric anhydride, acrylic anhydride and methacrylic anhydride. For example, it is well known that a phenol can be reacted using the Schotton-Baumann method with acyl halide in the presence of aqueous alkali or in the presence of pyridine using the Einhorn procedure. Thus, salicylic acid can be reacted with propionyl chloride or acryloyl chloride in the presence of aqueous sodium hydroxide or aqueous potassium hydroxide in a standard Schotten-Baumann method reaction.

The compounds of Formula I can also be made by ester interchange. For example, methyl acrylate and/or methyl methacrylate can be reacted with salicylic acid in the presence of a solvent such as benzene and a polymerization inhibitor. Appropriate catalysts for use in the present invention include, but are not limited to anhydrides, sodium acetate and sulfuric acid. Polymerization inhibitors, for use in the present invention, include, but are not limited to, 1,4-dihydroxybenzene, 4-tert-butyl-1,2-hydroxybenzene, 4-methoxyphenol, 2,4-dichloro-6-nitrophenol, 7-amino-1-hyroxynaphthalene, p-benzoquinone, 2,6-dichloro-4-benzoquinone, 1-amino-4-hydroxyanthraquinone, 1-naphthyl amine and divinylethyne.

As an alternative, methyl methacrylate (or methyl acrylate) can be transesterified with salicyclic acid in a solvent such as acetone, benzene or toluene in the presence of a polymerization inhibitor. In addition, the free acrylic acid or methacrylic acid can be reacted with salicylic acid in the presence of a catalyst. A polymerization inhibitor can be optionally added.

When R of Formula I is an aryl, such as phenyl, benzoylsalicylic acid or its sodium, potassium, calcium, lithium or ammonium salt can be formed. The synthesis procedure would be the same, that is, reacting salicylic acid with benzoyl chloride in the Schotten-Baumann method.

The compounds of Formula I can be used in treatment situations where the use of aspirin is indicated, (see, for example, Washington Post, Health Section, Jul. 25, 1989, pages 10–14).

The compounds of the present invention are for use in human medicine or veterinary medicine, such as in treating dogs, cats, horses and cattle.

The present invention also relates to pharmaceutical compositions comprising as the active ingredient, at least one compound of Formula I. The composition can be present in dosage unit form, for example, as a pill, capsule, tablet or gel tablet. The composition can further comprise other pharmacologically active materials, for example, aspirin, streptokinase, urokinase or tissue plasminogen activator (see Sarnoff, U.S. Pat. No. 4,661,469). The composition of the invention includes a pharmaceutically acceptable carrier or diluent, (See for example, Engel, U.S. Pat. No. 4,463,995, col. 13, line 35 to col. 15, line 54).

The dosage of the compounds of the present invention can be readily determined by one skilled in the art and, for example, range from 1 to 10 milligrams or even up to 1 gram. For example, in preventing heart attacks or as an analgesic there is used a dose of 325 milligrams of propionyl salicylic acid or acryloylsalicylic acid or 700 milligrams of stearoylsalicylic acid or oleoylsalicylic acid is administered to an average adult male. For preventing pre-eclampsia, there is used 50 milligrams of propionyl salicylic acid, acryloyl salicylic acid or methacryloyl salicylic acid or 125 milligrams of stearoyl salicylic acid or oleoyl salicylic acid. For children, there is used 60 to 70 milligrams of propionyl salicylic acid, acryloyl salicylic acid or methacryloyl salicylic acid or 150 to 175 milligrams of stearoylsalicylic acid or oleyl salicylic acid.

The dosage of the compound when given orally, such as in the form of a pill, generally will be higher than when the compound is administered intravenously.

The compounds of Formula I of the present invention are conventionally employed in pills or other solid formulation in an amount of about 0.5 to 5 mg/kg or even about 7 mg/kg body weight or in the case of higher molecular weight compounds, such as lauroyl salicylic acid, stearoyl salicylic acid or oleoyl salicylic acid, in an amount up to about 10 mg/kg of body weight.

As a first example, a capsule can be prepared by mixing about 500 grams of a compound of the present invention with about 175 grams of microcrystalline cellulose, about 315 grams of lactose and about 10 grams of magnesium stearate. About 100 mg of the mixture is, in each case, filled into solid size 3 gelatin capsules. One capsule contains about 40 mg of active material, such as propionyl salicylic acid or acryloyl salicylic acid.

As a second example, a tablet can be prepared comprising about 1 to 1000 mg, usually about 10 to 500 mg, of active material together with microcrystalline cellulose, starch and magnesium stearate. A typical formula for such a tablet follows:

| | |
|---|---|
| microcrystalline cellulose | 130 mg |
| modified starch | 20 mg |
| stearate | 5.5 mg |
| polyvinylpyrrolidone | 22 mg |
| stearic acid | 30 mg |
| propionyl salicylic acid | 300 mg |

As a third example, a tablet can be formulated as follows: about 8 kg of a compound of Formula I, such as propionyl salicylic acid or acryloyl salicylic acid, about 5 kg lactose and about 3 kg of microcrystalline cellulose are mixed with about 0.3 kg of polyvinyl pyrrolidone in about 12 kg of water. There is added about 3.45 kg of microcrystalline cellulose, about 2 kg corn starch, about 0.05 kg highly dispersed silica and about 0.2 kg magnesium stearate. The mixture is molded into a tablet weighing about 220 mg and having about a 9 mm diameter and a radius of curvature of about 13.5. Each tablet contains about 80 mg of active material.

In addition to the above-described use of the compounds of Formula I as an aspirin substitute, one skilled in the art will also appreciate that the compounds containing ethylenic double bonds can be polymerized using methods, cross-linking agents and free catalysts known in the art (see, for example, Guttag, U.S. Pat. No. 3,860,490, issued Jan. 14, 1975 and Steckler, U.S. Pat. No. 3,532,679, issued Oct. 6, 1970). For example, there can be employed azobisisobutyronitrile, e.g., in an amount of 0.05 to 1%, specifically 0.5% bound on the monomer, or there can be used the same amount of a peroxide, e.g., tert-butyl peroxide. Polymers thus formed can be used, for example, as an implant (the monomer leaching out into its environment over time). Alternatively, the polymer can be used with or without monomer in the preparation of a container, for example, a molded cup or a cup with a layer of polymer/monomer being present on the inner surface of the cup. In this embodiment, when the monomer is present it will leach out of the layer into the fluid contained within the cup. In addition, the polymer can be used in the construction of a contact lens using known methods (see, for example, Wichterle, U.S. Pat. No. 3,220,960, issued on Nov. 30, 1965). The lens can be constructed so as to include a compartment disposed within which is a pharmaceutical agent, for example, a compound of Formula I, which agent is released from the lens into its environment and potentially into the blood stream of the user.

In molding a cup, a lens or an implant, for example, there can be formed copolymers, e.g., a copolymer of methacryloyl salicylic acid (or acryloyl salicylic acid) with 0.02–10%, of a polyalkylene glycol diacrylate or dimethacrylate, e.g., 2% of ethylene glycol dimethacrylate.

All patents and publications mentioned herein are hereby incorporated by reference.

While the foregoing invention has been described in some detail for purposes of clarity and understanding, it will be clear to one skilled in the art from a reading of this disclosure that various changes in form and detail can be made without departing from the true scope of the invention.

What is claimed is:

1. A contact lens having a pharmaceutical agent releasably disposed therein wherein the lens itself comprises a polymer of an unsaturated carboxylic acid ester of salicylic acid, said unsaturated carboxylic acid having up to 24 carbon atoms and 1–4 ethylenic double bonds, or a pharmaceutically acceptable salt of said salicylic acid ester, and wherein the unsaturated carboxylic acid ester group is attached to the benzene ring of the salicylic acid through the phenolic oxygen atom.

2. A contact lens according to claim 1 wherein the lens is made of a polymer comprising acryloyl salicylic acid or methacryloyl salicylic acid units or a pharmaceutically acceptable salt of said salicylic acid.

3. A contact lens according to claim 1 wherein the unsaturated carboxylic acid contains 16 to 24 carbon atoms.

4. A contact lens according to claim 3 wherein the unsaturated carboxylic acid is erucic acid.

5. A contact lens according to claim 3 wherein the unsaturated carboxylic acid has 4 ethylenic double bonds.

6. A contact lens according to claim 2 wherein the polymer comprises acryloyl salicylic acid units.

7. A contact lens according to claim 2 wherein the polymer comprises methacryloyl salicylic acid units.

8. A contact lens according to claim 1 wherein the unsaturated carboxylic acid contains 1 ethylenic double bond.

9. A contact lens according to claim 8 wherein the unsaturated carboxylic acid contains 16 to 24 carbon atoms.

10. A contact lens according to claim 9 wherein the polymer comprises olcoyl salicylic acid units.

11. A contact lens according to claim 5 wherein the unsaturated carboxylic acid is arachidonic acid.

12. A contact lens according to claim 9 wherein the unsaturated carboxylic acid is selacholeic acid.

13. A contact lens according to claim 9 wherein the unsaturated carboxylic acid is palmitoleic acid.

14. A contact lens according to claim 1 wherein the unsaturated carboxylic acid ester of salicylic acid has the formula:

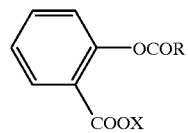

wherein R is an alkenyl group of 2 to 17 carbon atoms and X is hydrogen or a pharmaceutically acceptable salt thereof.

* * * * *

UNITED STATES PATENT AND TRADEMARK OFFICE
CERTIFICATE OF CORRECTION

PATENT NO. : 6,368,615 B1
DATED : April 9, 2002
INVENTOR(S) : Alvin Guttag

It is certified that error appears in the above-identified patent and that said Letters Patent is hereby corrected as shown below:

Column 6,
Line 45, "olcoyl" should be -- oleoyl --

Signed and Sealed this

Eleventh Day of June, 2002

*Attest:*

JAMES E. ROGAN
*Attesting Officer*     *Director of the United States Patent and Trademark Office*